(12) United States Patent
Selker et al.

(10) Patent No.: US 7,824,902 B2
(45) Date of Patent: Nov. 2, 2010

(54) OPTICAL INTERFACE FOR DISPOSABLE BIOREACTORS

(76) Inventors: Mark Selker, 27285 Elena Rd., Los Altos Hills, CA (US) 94022; Benjamin Blizard, 2442 Thaddeus Dr., Mountain View, CA (US) 94043; Timothy Johnston, 823 J St., Eureka, CA (US) 95501; Barbara Paldus, 12475 Skyline Blvd., Woodside, CA (US) 94062

( * ) Notice: Subject to any disclaimer, the term of this patent is extended or adjusted under 35 U.S.C. 154(b) by 570 days.

(21) Appl. No.: 11/725,255

(22) Filed: Mar. 17, 2007

(65) Prior Publication Data

US 2008/0171383 A1 Jul. 17, 2008

Related U.S. Application Data

(60) Provisional application No. 60/872,751, filed on Dec. 4, 2006, provisional application No. 60/856,563, filed on Nov. 3, 2006.

(51) Int. Cl.
*C12M 1/34* (2006.01)
(52) U.S. Cl. .................. 435/288.7; 356/417; 250/461.2
(58) Field of Classification Search ............. 435/288.7; 356/417; 250/461.2
See application file for complete search history.

(56) References Cited

U.S. PATENT DOCUMENTS

| 1,523,864 | A | * | 1/1925 | Corey ........................ 222/401 |
| 5,750,337 | A | * | 5/1998 | Squirrell ........................ 435/6 |
| 5,810,469 | A | * | 9/1998 | Weinreich ................... 362/298 |
| 2008/0032389 | A1 | * | 2/2008 | Selker et al. ............. 435/283.1 |

* cited by examiner

*Primary Examiner*—William H Beisner
*Assistant Examiner*—Michael Hobbs
(74) *Attorney, Agent, or Firm*—Herbert Burkard

(57) ABSTRACT

A port assembly for use with a polymeric bioreactor bag includes the following components:
  i) a hollow port member made from a material which can be fusibly affixed to the wall surface of the bioreactor bag;
  ii) at least one fluorophore spot positioned on the port member;
  iii) a conduit for conveying excitation light from an optical source to the fluorophore, which conduit can be a lens, a curved parabolic collimator, a shaped reflector or a wave guide; and
  iv) a second conduit for conveying fluorescent emission light from the excited fluorophore to a photo-detector, which second conduit although different from the first, can likewise be a lens, a curved parabolic collimator, a shaped reflector or a wave guide.

15 Claims, 11 Drawing Sheets

OPTICAL INTERFACE FOR DISPOSABLE BIOREACTORS

RELATED APPLICATIONS

This application claims priority from commonly assigned applications Ser. No. 60/872,751, filed Dec. 4, 2006 and 60/856,563 filed Nov. 3, 2006

FIELD OF THE INVENTION

This invention relates to an improved method and apparatus for measuring analyte concentration in disposable bioreactors.

BACKGROUND OF THE INVENTION

It is known that to obtain optimal yields in bioreactors and fermentors active monitoring and control of basic environmental factors is necessary [James Lee, *Biochemical Engineering*, Washington State University, e-book, 2002]. The most critical of these factors include temperature, dissolved oxygen level, and pH. The dominant paradigm for monitoring these quantities in stainless steel or glass tank type bioreactors and fermentors has been through the use of electrochemical probes. Despite some of the drawbacks associated with this type of probe, they have proven to be acceptable in performance level and currently enjoy widespread use in glass and steel bioreactors/fermentors.

However, recent years have seen the rise in popularity of disposable bioreactors fabricated of bio-compatible polymers to supplement, or in many cases replace glass and stainless steel bioreactors. A major issue has been the ability to continuously and reliably provide on-line monitoring of pH and dissolved oxygen for these disposable (polymeric) bioreactor vessels. Part of the issue is that it has been difficult to successfully implement electrochemical probes with disposable bioreactors. The main issues with the use of electrochemical probes are three fold:

1. Size;
2. Electrical grounding issues.
3. Inability maintain a sterile system.

The majority of disposable bioreactors currently sold are comprised of flexible, biocompatible (USP, FDA regulation compliant, and animal product derived free) polymers. There is often difficulty in mounting rigid glass and steel probes to the polymeric bioreactor surfaces which flex dynamically in operation. Methods to circumvent this problem have been attempted, but inserting the probes into disposable bioreactors while maintaining the sterility and integrity of the seal remains problematic, especially for smaller bag reactors. Additionally, electrochemical probes are prone to grounding issues and electrical ingress noise when used with a polymeric, non-conductive, disposable bioreactor. In a traditional stainless steel bioreactor, these factors are typically not a concern as the probes are in contact with the metal wall of the bioreactor, which can be grounded. However, when the bioreactor is made solely or predominantly of a flexible, dielectric (polymeric) material such as low density polyethylene, polypropylene, or ethylene-vinyl acetate (EVA) it is difficult to provide the requisite shielding and grounding. Most importantly, much of the appeal of single use bioreactors is the ability to eliminate time consuming work and capital infrastructure associated with sterilization, and cleaning as compared to a traditional metal or glass bioreactor. Users of disposable bioreactors would strongly prefer to receive a pre-sterilized (typically with Gamma or Beta radiation) bioreactor with calibrated probes in place and filled with media and simply start their process. Inserting anything into the already sterilized disposable bag reactor adds another layer of uncertainty and effort. We have found that optical technology based probes can address many of the aforementioned issues.

In recent years, disposable bioreactors have proliferated, and can now be found in many shapes and sizes. Some of the incipient work in making the disposable bioreactor a commercial reality was done by Wavetech. Their bioreactor is based on a disposable bag (often referred to as a rocker bag or a pillow bag) made of polyethylene and/or other suitable biocompatible plastic. The bag sits on a device that rocks the bag back and forth to both mix and oxygenate the contents. The espoused theory is that this motion is similar to waves in the ocean and is therefore beneficial to water based life in general. (See U.S. Pat. No. 6,190,913, Singh, Vijay, Method for Culturing Cells Using Wave-induced Agitation). A similar approach was taken by Applikon for its Appliflex product, and Metabios for its Optima product. Hyclone and Xcellerex have developed a different style of disposable bioreactor based on a disposable liner which sits inside a rigid container vessel and seeks to mimic the behavior of a traditional bioreactor. Specifically, a stainless steel container, or other rigid structure that serves as external support, is lined with a disposable biocompatible plastic membrane and uses a traditional impeller mixing system.

A method of monitoring critical bioprocess parameters such as dissolved oxygen and pH that addresses some of the existing issues with disposable bioreactors is provided by the use of fluorescent optical sensor materials [Wolbeis, O. S., *Fiber Optic Chemical Sensors and Biosensors*, Vol 1&2 CRC, Boca Raton, 1991.]. These fluorescent optical sensor materials operate on the principle of dynamic quenching [Lakowicz, *Principles of Fluorescence of Spectroscopy*, $3^{rd}$ edition, Springer 2006]. The currently preferred term for these materials is fluorescent dye, indicator dye or fluorophore and such terms will be used interchangeably hereinafter. The fluorescent lifetime of substances such as organo-metallic fluorophores or Pt metal group based fluorophores is quenched, or shortened, by contact with the analyte under study. Dissolved oxygen is a natural analyte to measure using this method, as oxygen is known to readily quench the fluorescence of many fluorescent dyes. However, in addition to $O_2$ fluorophores suitable for the detection of other analytes such as, $CO_2$, pH and glucose are known in the art. Therefore, pH, $CO_2$, and glucose sensors can be constructed using this technology and suitable fluorophores. Despite the fact that the fluorescence quenching effect was discovered by Kautsky in 1939 [Hans Kautsky, *Quenching of Luminescence by Oxygen*, Trans. Faraday Soc., 1939, 35, 216-219] it has taken more than 60 years for this technology to evolve to a level where it is suitable for biotechnology based instrumentation.

Another similar area of interest for use in monitoring bioreactors is the use of auto-fluorescence. In some instances, it is desireable to use visible and ultra-violet wavelength excitation to exploit naturally occurring fluorescence behavior to detect the presence of analytes or cell characteristics of interest. For example, many known metabolic markers such as NADH, FAD, and tryptophan, are known to auto-fluoresce and can be utilized in accordance with the teaching of the present invention to give information regarding cell viability and cell energy.

Despite the promise of this optical technology, it faces a fundamental issue due to the fact that many indicator dyes (fluorophores), especially those based on porphryins, tend to photo-degrade. This photo-degradation is often termed static quenching and is due to the fact that in their excited states fluorophores often react to form the photo-stable ground states of other non-fluorescing compounds. This behavior causes a fundamental change in the optical response characteristics of the fluorescent dye and can lead to a loss in signal level and to calibration error or signal drift. Significant effort has been put forth in an effort to understanding the degradation mechanisms, and how to mitigate them. Several strategies have been suggested [P. S. Dittrich and P. Schwille, Photobleaching and stabilization of fluorophores used for single-molecule analysis with one and two photon excitation, Applied Physics B 73, 829-837, 2001, Sandra Bencic-Nagale and David R Walt, *Extending the Longevity of Fluorescence-Based Sensor Arrays Using Adaptive Exposure*, Anal, Chem., 77, 6155-6162, 2005 However, the most straight forward solution is to limit the total fluence (energy×time) or photon exposure to which the photo-sensitive fluorophores are subjected. This solution is achieved by the present invention and is addressed in detail hereinafter.

The common thread among all existing types of disposable bioreactors is that, as previously indicated, they utilize a biocompatible dielectric material which is intended to be discarded after a single use. These biocompatible materials are generally translucent, but not transparent in the visible region of the optical spectrum. In fact, reactions between room light and the dielectric materials have motivated many vendors to provide more or less opaque covers for the bioreactor. The basic point is that the transmission of light through these disposable products is not a property specifically desired or engineered into them. Additionally, disposable bioreactors are often constructed as a composite, multi-layer structure in which an inner layer comprising polyethylene, polypropylene, or EVA, is combined with an outer layer comprising nylon, Teflon, or another material depending on whether strength, oxygen permeability or other specific characteristic is most desired. Irrespective of the precise reason for the layering, the end result is that the optical transmission properties of the bag are significantly compromised. The importance of this issue to the implementation of fluorescent optical sensors will be discussed shortly, but it is necessary to first review some of the basic principles which govern the operation of fluorescence based optical sensors.

The dynamic quenching of fluorescence is described to first order by the Stern Volmer equations:

$$\frac{I_0}{I} = 1 + K_{SV} pO_2$$

$$\frac{\tau_0}{\tau} = 1 + K_{SV} pO_2$$

$$K_{SV} = k \, \tau_0$$

Equations 1

Where I is the fluorescence intensity, $I_0$ is the fluorescence intensity in the absence of oxygen, $\tau$ is the fluorescent lifetime, and $\tau_0$ is the fluorescent lifetime in the absence of oxygen, $K_{SV}$ is the Stern Volmer constant, and k is the bi-molecular quenching constant.

These equations and the physical process they describe are the basis for how these sensors indicate the change in concentration of the species (i.e., analyte, quencher) under study. Using this principle it is possible to sense the change in intensity or lifetime of the fluorophore which comes in contact with the quencher species of interest. For example, in the absence of the quencher the lifetime of the fluorophore will be at its longest and the fluorescent intensity therefore at its highest. As the concentration of the quencher increases, both the fluorescent lifetime and the fluorescent intensity decay. For a number of reasons, including cost and simplicity, sensing the change in the lifetime in the frequency domain is the dominant methodology for current commercial instrumentation. In contradistinction, in the implementation of the present invention, the change in lifetime is sensed through a change in the phase delay of the fluorescent radiation, as compared to the excitation emission [See J. Lakowicz, *Principles of Fluorescence Spectroscopy*]. A light source, at a wavelength at which the fluorophore (frequently, but not necessarily an organo-metallic compound) absorbs, is modulated and the emitted light is monitored. The emitted light is typically analyzed using phase sensitive detection systems such as a lock-in amplifier to examine the phase delay between the excitation source and the emitted radiation.

In the simplest case, this change in phase can be expressed as:

$$\phi = \text{ArcTan}(2\pi f \tau) \quad \text{Eq. 2}$$

Where f is the modulation frequency of the excitation source, and $\tau$ is lifetime of the fluorophore as described by the Stern Volmer equations. (Equations 1)

A prior art approach for implementing the aforementioned phase delay analysis is shown in FIG. 1. This design uses fiber optic delivery of the excitation light, as well as fiber based collection of the fluorescence signal.

In FIG. 1, 1 is the excitation light such as an LED, which is normally sinusoidally modulated, 2 is an optical filter which tailors the optical excitation spectrum such that it is matched to the absorption feature of the fluorophore 6. This absorption feature, and hence the excitation spectrum will vary depending on the exact fluorophore used and the matrix in which it is complexed. In general, it is advantageous to use the longest wavelength (lowest energy) photons that will excite the fluorophore. Component 3 is a fiber optic coupler which allows the excitation light to travel to the common delivery/collection fiber 4, while allowing the fluorescent signal to simultaneously travel in the opposite direction. This fluorescent signal passes through filter 7 which is designed such that only the fluorescent signal reaches the optical detector 8; i.e., any pump light or ambient light is blocked from reaching the detector. An optional set of coupling optics is shown in the design of FIG. 9 which helps increase collection and delivery of light from and to the fluorophore, respectively.

A key issue in fluorescent optical probes is the trade-off between the signal-to-noise ratio ("SNR") and photo-degradation of the fluorophore. The higher the excitation light power level the better the signal to noise ratio, but the more rapid the photo-degradation rate of the fluorophore. It therefore follows that effective collection of the fluorescent photons can play a big part in controlling the photo-degradation rate. Specifically, the more efficiently the fluorescence is collected, the higher the SNR and therefore the lower the required intensity of the excitation light. Likewise, the lower the intensity of the excitation light source, the slower the photo-degradation rate. This is important, because in fiber optic based systems of the prior art as described above, a large percentage of the fluorescent signal light is not utilized due to the etendue (as described below) limitations of optical fiber based designs.

In the branch of optics known as radiometry, the concept of brightness or etendue is very important because it is a conserved quantity. Etendue is expressed as:

$$S = A\Omega \quad \text{Eq. 3}$$

Where S represents the etendue, A is area of the light source or detector, and Ω is the solid angle that the source emits into, or that it is collected by the detector.

Brightness is the optical power divided by the etendue and this is a fundamental conserved quantity. It is therefore impossible to increase the brightness of a source using passive optical elements [See Ross McCluney, *Introduction to Radiometry and Photometry*, Artech House, 1994]. The relevant issue for fluorescent optical sensors, and in particular, fiber optic based fluorescent optical sensors is that due to the limited modal area of the fiber and its limited acceptance angle or numerical aperture the etendue is fundamentally limited.

In a typical plastic optical fiber used for the collection of light, the mode field diameter can be as large as 1 mm with a numerical aperture of 0.63. A numerical aperture of 0.63 means that the half angle of acceptance of the fiber is Arcsine (0.63) i.e., approximately 39 degrees—or a full angle of 78 degrees out of the total of 180 degrees in the half plane. However, the fluorescent material is typically in the form of a thin disk or dot which is 3-5 mm in diameter and emits into all space with Lambertian characteristics (e.g., an intensity that has a $\cos(\theta)$ dependence and where $\theta$ is the angle between the normal to the disk and the angle of emission of the photon). Conservation of brightness tells us that therefore only a very small percentage of the emitted fluorescent light can be collected by the fiber. Since it is difficult to integrally and seamlessly integrate optically transparent materials to the plastic bioreactor bag further loss can occur.

1. The fiber tip is not located very close to the fluorescent material or if the fluorescent material is located on the other side of a diffusive material (e.g. a multi-layer bag, or a textured bag material); and/or
2. If the distance and orientation of the emitter and receiving fiber is not fixed. Therefore, either of these conditions will lead to further deterioration of the coupling efficiency.

The issues described above are typical of the issues encountered when fiber optic based delivery and collection systems are used with fluorescent sensors on disposable bioreactors. These issues can lead to decreased performance and reliability, while simultaneously increasing the photo-degradation rate of the fluorophore. Often the photo-degradation rate in fiber optic based designs is higher than other designs as the excitation intensity level is increased to make up for collection shortfalls. It is possible to mitigate some of these effects by either maximizing the light collection efficiency, and/or by using a larger area of fluorophore (i.e., a larger fluorescent dye spot) and simply generating and collecting more photons irrespective of the efficiency. Specifically, if the fluorescent dye spot is larger, then the illumination intensity can remain the same or perhaps even be lowered and the optical collection efficiency can remain the same, yet produce a higher fluorescent signal level. The brightness of the fluorescent source as described by equation 3 has not been improved, but a higher signal level is obtained at the cost of using a larger area. When using an optical fiber to receive and/or illuminate the fluorophore, the usable spot size is inherently limited by the fiber diameter.

BRIEF DESCRIPTION OF THE INVENTION

The ability to create an optical interface which allows the end-user to employ reliable, low drift, disposable sensors while simultaneously maintaining sterility is advantageous to the user of a disposable bioreactor. This is true irrespective of whether the light is delivered by optical fiber, by brightness conserving optics, or by an optical system using one or a plurality of optical elements. An optical interface in accordance with the present invention allows the use of a plurality of optical delivery and collection systems and also allows the user to sterilize the optical system for future use. A preferred embodiment provides a port/attachment site on the bioreactor bag which permits the end user to select and subsequently install the optical illumination and collection system (henceforth referred to as a "reader"). In particular, the present invention provides a port design which can be pre-fabricated as part of the bioreactor bag and permits the end user to subsequently choose, at the use site, the correct fluorophore for the particular analyte to be detected (e.g., $O_2$ or pH) and also the particular optical design and configuration of the reader and install same in the port.

BRIEF DESCRIPTION OF THE DRAWINGS

FIG. 2 shows a port assembly utilizing a fiber optic based system that addresses many of the shortcomings of the prior art technology.

FIG. 3 shows how the port of FIG. 2 sits in the floor of a disposable rocker-type bag reactor.

FIG. 4 shows a curved parabolic collimator (CPC) which can be used to collect the fluorescence signal in some embodiments of the present invention.

FIG. 5 shows a waveguide to deliver the excitation light. This allows the photo-detector to be in contact with the fluorophore spot and thereby maximizes collection efficiency when used in other embodiments of the present invention.

FIG. 6 shows an optical system where the LED excitation beam is shaped by a reflective optical element.

FIG. 7 shows a port design in accordance with the present invention for affixing the optical components (in this case a CPC) to the polymeric bioreactor bag wall.

FIGS. 2 and 7 show embodiments of the present invention wherein the port and the major optical components can be fixedly mounted on the bioreactor bag wall.

In FIGS. 8 and 9 are illustrated alternative embodiments of the present invention in which the port is substantially integral with the bioreactor bag wall, but the optical components can be subsequently installed by the end user when desired.

FIG. 8 shows a port and disposable component that enables on demand customization of the sensors using either free space or optical elements (e.g. lenses, mirrors)

FIG. 9 shows a port and a disposable component similar to that of FIG. 8 that allows for customization as well as the use of a fiber based delivery and collection system.

DETAILED DESCRIPTION OF THE INVENTION

Figure 1:
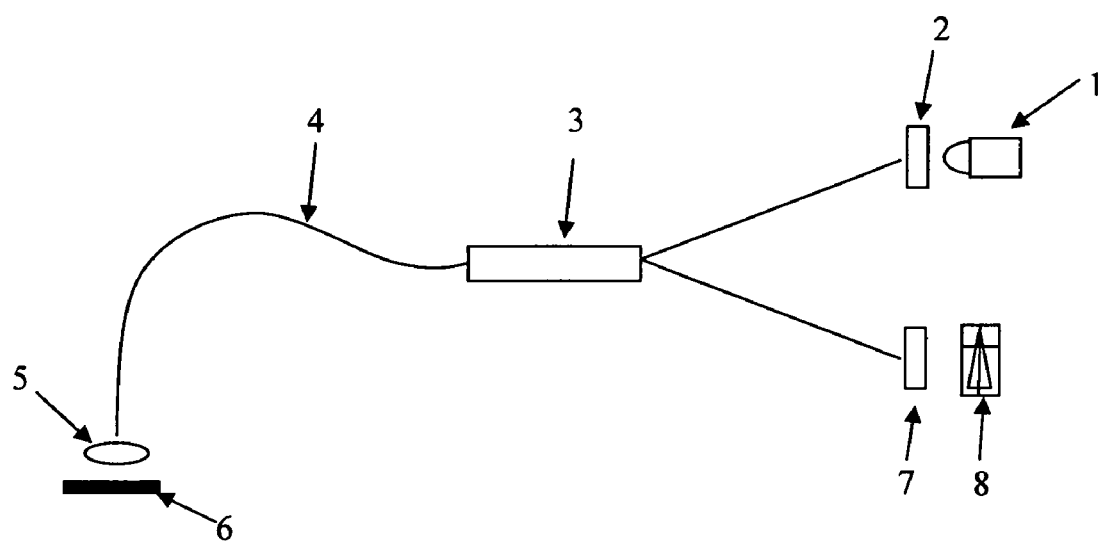
FIG. 1 shows a prior art design of a fiber optic based system for measuring fluorescence quenching.
Figure 2:
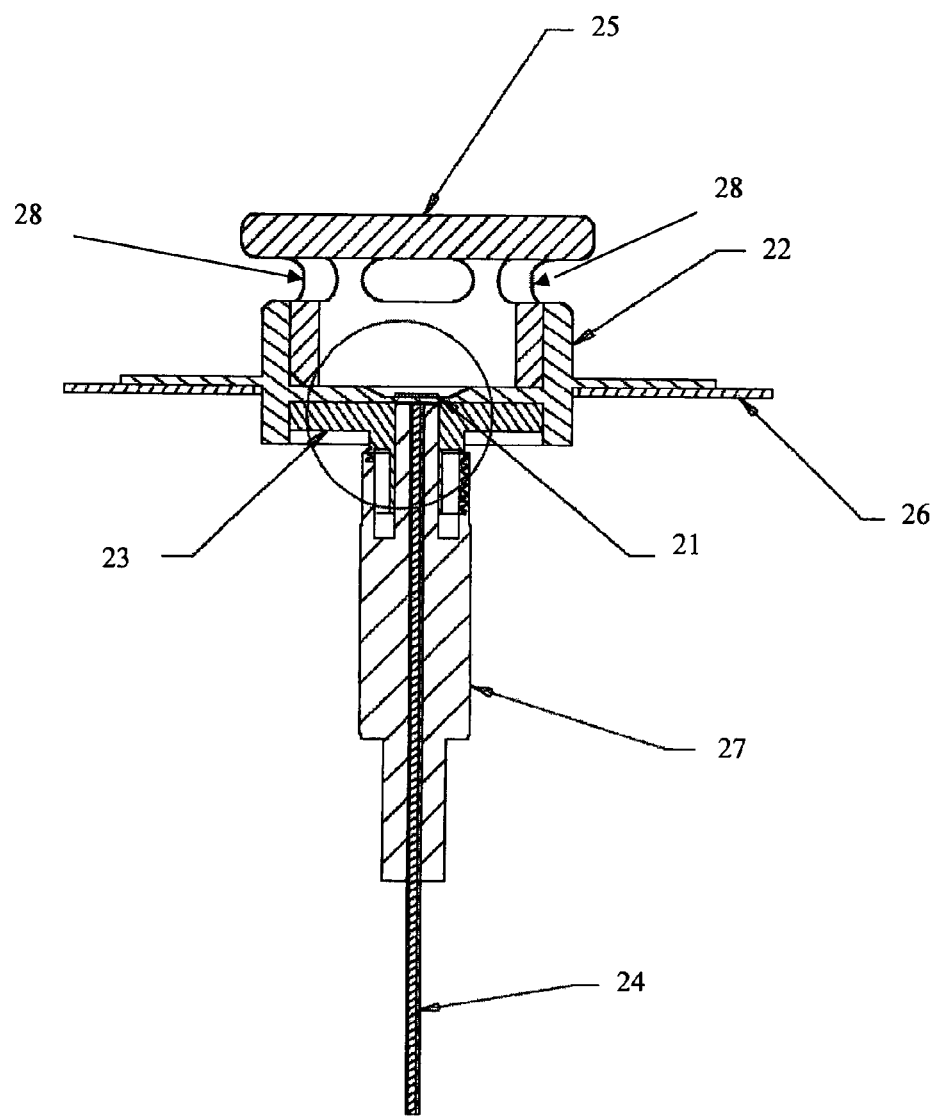
FIGS. 2 through 8 show various components or embodiments of the present invention.

Despite their inherent limitations, it is sometimes advantageous to utilize fiber optic delivery and/or collection systems with disposable bioreactors. A method and port assembly apparatus in accordance with the present invention that enable the reliable use of fibers in this application are depicted in FIG. 2. In FIG. 2, 21 is a fluorophore (e.g.: an oxygen sensitive fluorophore), 22 is an optically translucent (and preferably biocompatible) material such as polyethylene. This hollow port member is thermally or RF welded into the bioreactor's polymeric wall surface 26. 24 is the fiber optic cable, and 25 is a foraminous shield fitted to port 22 that prevents ambient light from directly impinging upon the fluorophore and thereby causing drift in the reading through accelerated photo-degradation. However orifices 28 in the shield allow the fluid contents of the bioreactor bag to contact the fluorophore and thereby decrease the fluorophore emission strength by quenching. Additionally, if used in a bag type bioreactor—since the fluorophore sits on the bottom of the port it will remain covered by the fluid contained within the bioreactor even if it is rocking or shaking. The fiber optic cable, 24 is shown locking to a ferrule, 27, which advantageously forms part of the port assembly. The fiber can utilize a single fiber optic cable, or multiple fibers or fiber cores. An advantageous aspect of the embodiment shown is that the fiber optic delivery system is rigidly attached to the disposable bioreactor wall surface which leads to improved measurement reproducibility by simultaneously controlling the separation distance between the optical fiber and the fluorescent dye. Furthermore, in this configuration the optical quality of the material interposed between the fluorescent sensor and the fiber (i.e., the material of which port 22 is fabricated) can be chosen to optimize performance. Optimization means that the transmission is maximized by controlling the thickness and surface quality of the interposed material such that collection of the fluorescent signal is maximized. This approach mitigates, to the maximum extent possible, many of the issues inherent with prior art fiber optic systems. It is also possible to utilize additional optics or an arbitrary size spot with the design in FIG. 2 in order to increase the collected fluorescent signal power. It should be noted here that this style of port will optimally be affixed to the disposable bioreactor in a location where it is always in contact with the bioreactor fluid in order to allow continuous sensing of the target analyte in question.

While fiber optics can often enable a more convenient design, it is frequently preferable not to use optical fiber to either deliver the excitation light to the fluorophore or to collect the fluorescence signal. As previously described, inherent to the use of fiber optics is a imitation in collection efficiency resulting from the principle of the conservation of brightness. Furthermore, transmitting the excitation light and collecting the fluorescent signal via fiber optic cables introduces another variable. Specifically, fiber optic cables will not guide radiation completely if bent beyond a certain limit which can make the sensing system more prone to erroneous readings, drift or failure. We have developed an alternative method to maximize the collection of the fluorescence signal by utilizing etendue conserving optics at the bag interface itself. This alternative embodiment of the present invention eliminates the brightness limitations imposed by the use of optic fiber, and hence reduces the photo-degradation rate. For example, we have discovered it is possible, and indeed advantageous, to use a curved parabolic collimator ("CPC") to collect the fluorescence such that virtually the entire fluorescent signal impinges upon the photodiode detector.

Figure 3:
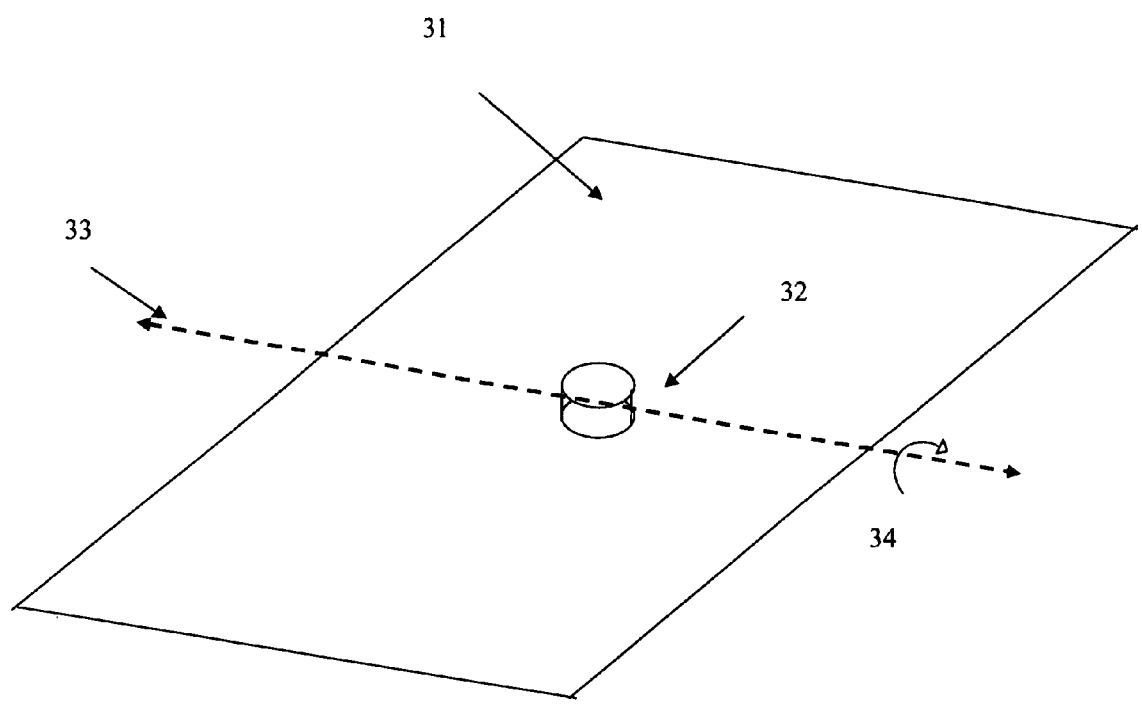

FIG. 3 shows the bottom of a typical pillow or rocker style bag. The port design of FIG. 2 is shown in outline form 32 affixed to the bottom of the bag 31. This style of bag would be rocked around an axis 33 running through the center of the bag as depicted by the arrow 34. The port 32 can be placed anywhere along the center of the bag and as long as the walls of the port are high enough, or the rocking angle shallow enough, the fluorophore will always be in contact with the fluid and hence will always be measuring the analyte concentration in the bioreactor fluid as opposed to the air.

Figure 4:
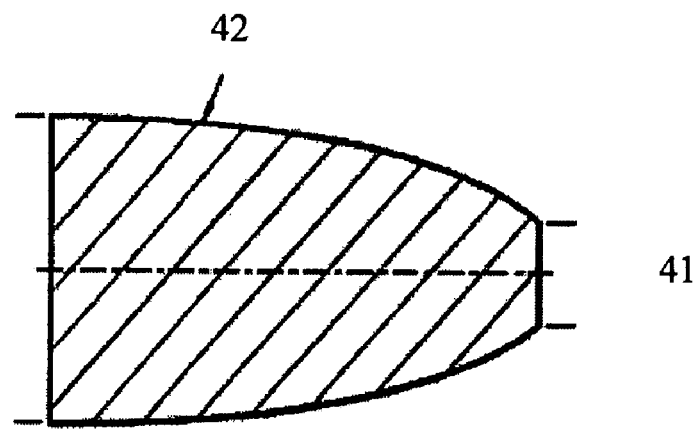

The CPC shown in FIG. 4 is constructed utilizing the general principles described by Welford and Winston [*Nonimaging Optics*, by: Roland Winston, Juan C. Min~tano, Pablo Benitez, with contributions by Narkis Shatz and John C. Bortz, Elsevier Academic Press, 2005.] This design uses principles from geometric optics and the edge-ray principle to optimize the collection of the fluorescent signal. A CPC acts to conserve etendue such that spatial extent is traded off for angular distribution. A typical CPC collects light within a small angular range and a large area and transforms that light to a small spot with a large angular range. In our invention, however, the CPC is used in reverse from the typical application i.e., it collects fluorescent light from the dot, which has a relatively small area and a large angular range. The CPC then directs that light to a larger area having a small angular range. This use of etendue allows us to efficiently capture the fluorescent signal on a standard photo-detector. After receipt by the photo-detector, the signal is preferably amplified and sent to a transmitter together with the electronics required to interpret the signal, and, if desired, display and/or record same.

The profile and end views for a CPC when used with e.g., a 3.6 mm diameter Lambertian source (fluorescent spot) collected into a 30 degree angular range is shown in FIG. 4. The CPC is designed to collect and collimate the light from a specific light source that it is paired with. In our example, the CPC approximately collimates the 3.6 mm Lambertian emitter shown in FIG. 3. Based on the index of the material used, the size of the spot, 41, and the radiation pattern emitted by the spot—the CPC wall curvature, 42, is constructed according the art taught by Welford et al.

Another optical solution in accordance with the present invention that does not rely on fiber optic utilizes a slab waveguide. Slab type waveguides can be used to deliver the excitation light to the fluorophore, while also allowing optimization of the collection geometry as described below. The waveguide embodiment of the present invention provides at least two significant benefits: uniform excitation and a high collection efficiency. Uniform excitation is accomplished by confining light having a large angular distribution within a (normally plastic) waveguide. As the light travels within the waveguide, components traveling at different angles overlap spatially or mix. Such waveguides are preferably designed using optical ray tracing simulations and procedures known to the skilled artworker such that a high degree of spatial mixing or uniformity of the beam occurs. When the light traveling in the waveguide becomes spatially uniform it can provide uniform excitation light to the fluorescent material. We have found that for a specific waveguide thickness, length and index of refraction, such uniform excitation can be achieved. With this design a high collection efficiency can be accomplished by placing a detector close to the fluorescent material. The details of this wave guide optical design are shown in FIG. 5.

Figure 5:
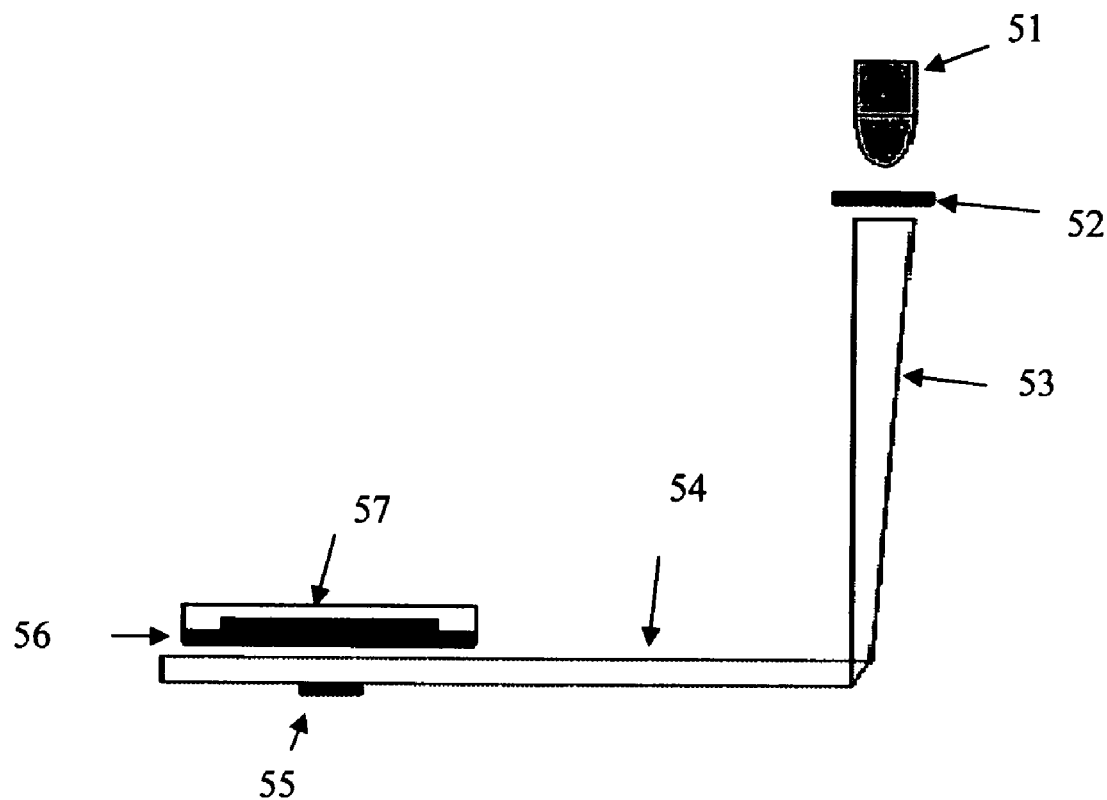

In FIG. 5, 51 is the excitation light source e.g., an LED, 52 is the optical filter which shapes the excitation spectrum to match the fluorescent dye absorption spectrum and prevents potentially damaging ultra-violet light from impinging on the fluorescent material 55, while 53 and 54 are waveguides which enable the excitation light to travel from the LED to the fluorescent material 55, while simultaneously allowing spatial mixing to occur such that the light that impinges on the fluorescent material 55 is uniform. A second optical filter 56 can advantageously be used to ensure that substantially only the fluorescent signal reaches photo-detector 57.

Figure 6:
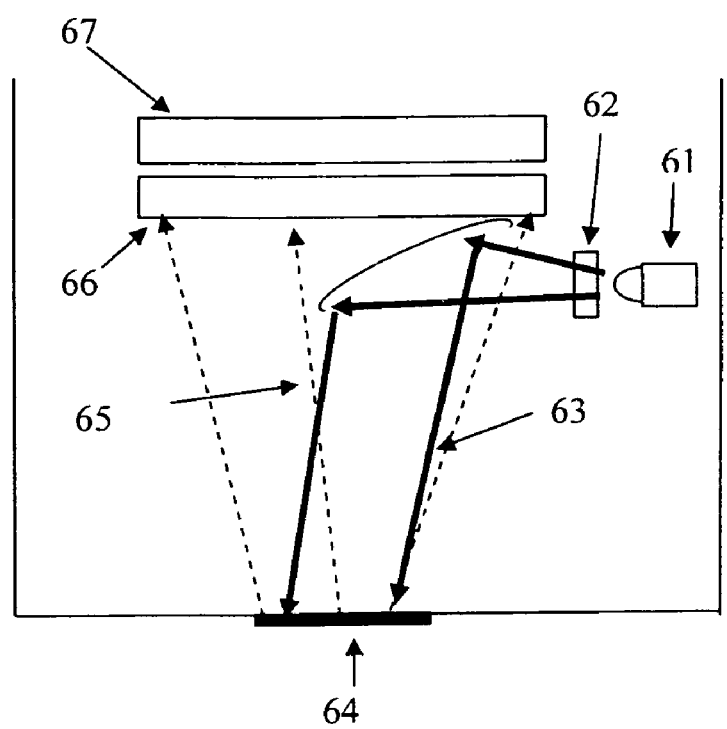

Both the CPC and slab waveguide optical systems can be integrated into single use/disposable bioreactors by integrating a port or similar mounting system into the bioreactor. The port shown in FIG. 6 is similar in configuration to the port for the fiber based mount shown in FIG. 2. This port is also constructed of a (normally biocompatible) dielectric material and allows the optical subsystem to be securely affixed to the bioreactor. Additionally, the port allows the integration of optically transparent biocompatible materials on which to mount the fluorescent material. This means that the optical signals do not have to travel through translucent material and either the CPC or waveguide based optical transmission and receiving systems can be implemented as shown and described. The major difference between the designs shown in FIG. 2 and FIG. 5 is that the fiber based collection method has been replaced with the above described internally mounted CPC, although, alternatively, a slab waveguide, or any other optical assembly that efficiently collects light can be implemented instead (e.g., a lens or combination of lenses).

In FIG. 6 a phase fluorometric system is depicted where the optical excitation light is collected by a reflective optical element. In this FIG. 61 is the optical source (preferably an LED), and 62 is an optical filter which passes the part of the spectrum that is matched to the fluorophore's 64 absorption spectrum. This filter will generally block UV light which might increase the rate of photo-degradation of the fluorophore spot. The filtered excitation light 63 impinges upon the fluorophore 64. The emitted fluorescent signal 65 passes through another optical filter 66 which removes substantially or totally light other than that emitted by the spot. This light finally impinges upon a suitable detector or photodiode. The entire assembly or parts of the assembly can be contained in a hollow port member comprised of a biocompatible FDA and/or USP compliant, animal component derived free material.

Figure 7:
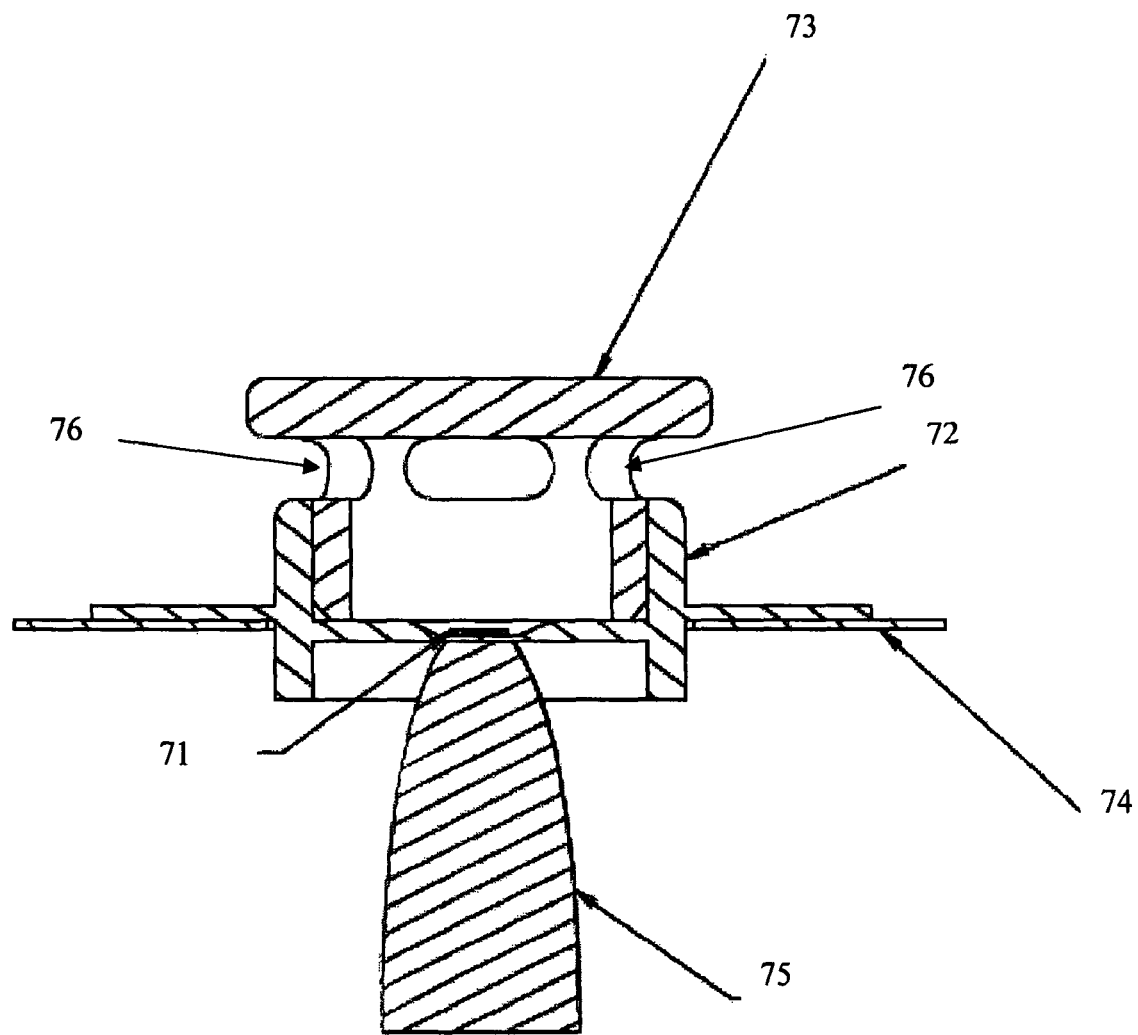

In FIG. 7, 71 is an oxygen sensitive fluorescent dye, 72 is a preferably biocompatible FDA and USP regulation compliant, animal component derived free material which comprises a hollow port member which is thermally or RF fused to the bioreactor's lining 74. The ambient light shield is shown as 73, while 75 denotes the CPC. It should be noted that for this embodiment, as in FIG. 2, the port should advantageously be placed in the disposable bioreactor such that the fluorophore is always in contact with the bioreactor's fluid. This is achieved as a result of the orifices 76 in the shield 73. For a bag type bioreactor, this will typically be in the center and at the bottom of the bag.

Figure 8:
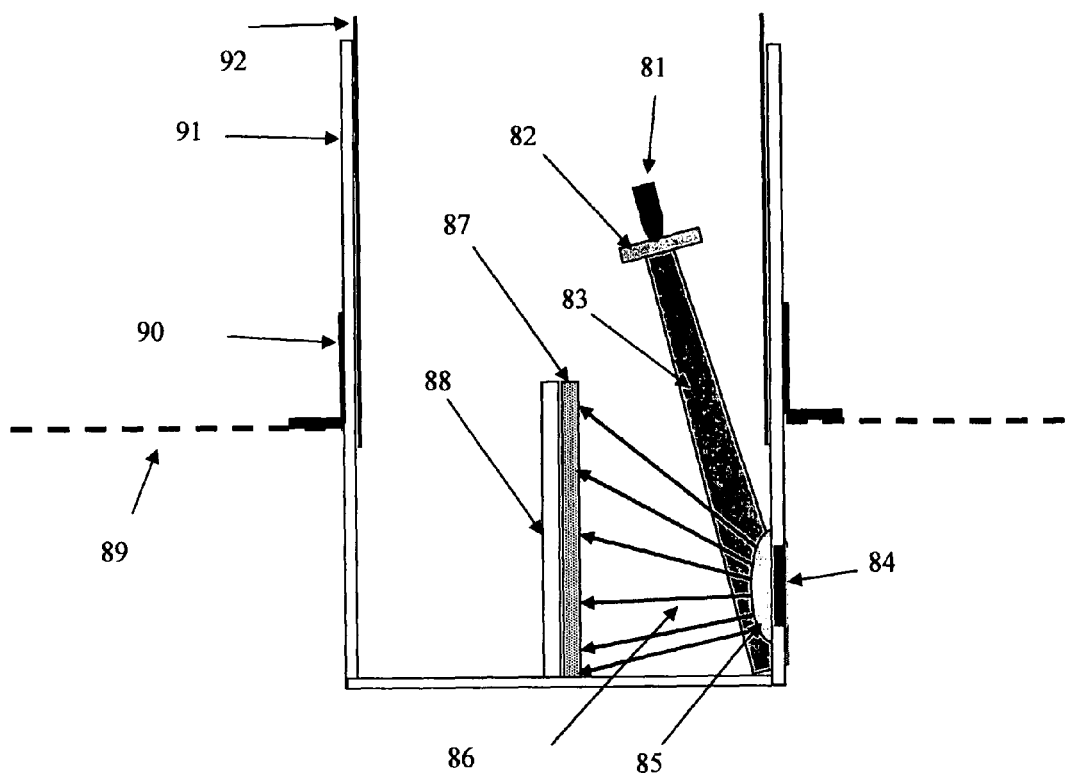

Another method of providing an optical interface that facilitates the use of disposable fluorescence sensor technology is to utilize a port affixed to the wall of the disposable bioreactor. The disposable components of the fluorometric sensor can be inserted into the port and secured against leakage. The disposable components are generally comprised of the fluorescent dye spot; an optical assembly which helps collect the fluorescent signal and the shell or port which holds the aforementioned components. An embodiment is shown in FIG. 8 where 81 is the light source, (preferably an LED) and 82 is a filter which shapes the optical spectrum of the excitation light. For example, if the LED emits any light in the UV range it is often preferable to prevent this light from reaching the fluorescent dye. Additionally, it is not necessary to illuminate the spot in the spectral region where the fluorophore does not absorb. Only filtered excitation spectrum, 83, impinges on the fluorophore, 84. The fluorophore emits (fluoresces) and a lens 85 or other optical collection device (e.g. CPC) is use to help guide the fluorescent signal 86 to a second optical filter 87. This filter is comprised of a dielectric stack or absorptive glass, or a combination thereof and allows only light in the wavelength band of the fluorescent signal to impinge upon the optical detector 88. This optical detector can, for example, be a PIN photodiode, an avalanche photodiode, a photomultiplier tube or other suitable detector. In general, the excitation source 81, filter 82, photo-detector 88 and filter 87 (together with a supporting/mounting structure that fits within the disposable optical component will form part of a non-disposable component unit 92 commonly referred to as a "reader"). Reader 92 will normally be inserted into a (hollow port member (disposable shell 91) which is preferably comprised of a suitable USP and FDA regulation compliant material, i.e., one that is animal derived product free, optically transparent and moldable or machinable. The disposable shell 91 can house the lens 85 and will have the fluorophore spot 84 deposited on or otherwise affixed to its exterior. The disposable shell 91 is inserted into a port 90 which is attached to the disposable bioreactor lining 89. An important feature of this design is that the port 90 can be made to house a traditional electrochemical sensor (which is normally 12 mm in diameter), or can alternatively be used with a disposable shell in accordance with the teaching of the present invention. Additionally, the disposable shell can be optionally inserted into ports so that the disposable bioreactor's sensing capabilities can be customized to a user's particular sensor requirements on demand and at the appropriate time in the manufacturing process. This allows the disposable bioreactor manufacturer to have a more general product with the customization occurring later in the order administration process.

Figure 9:
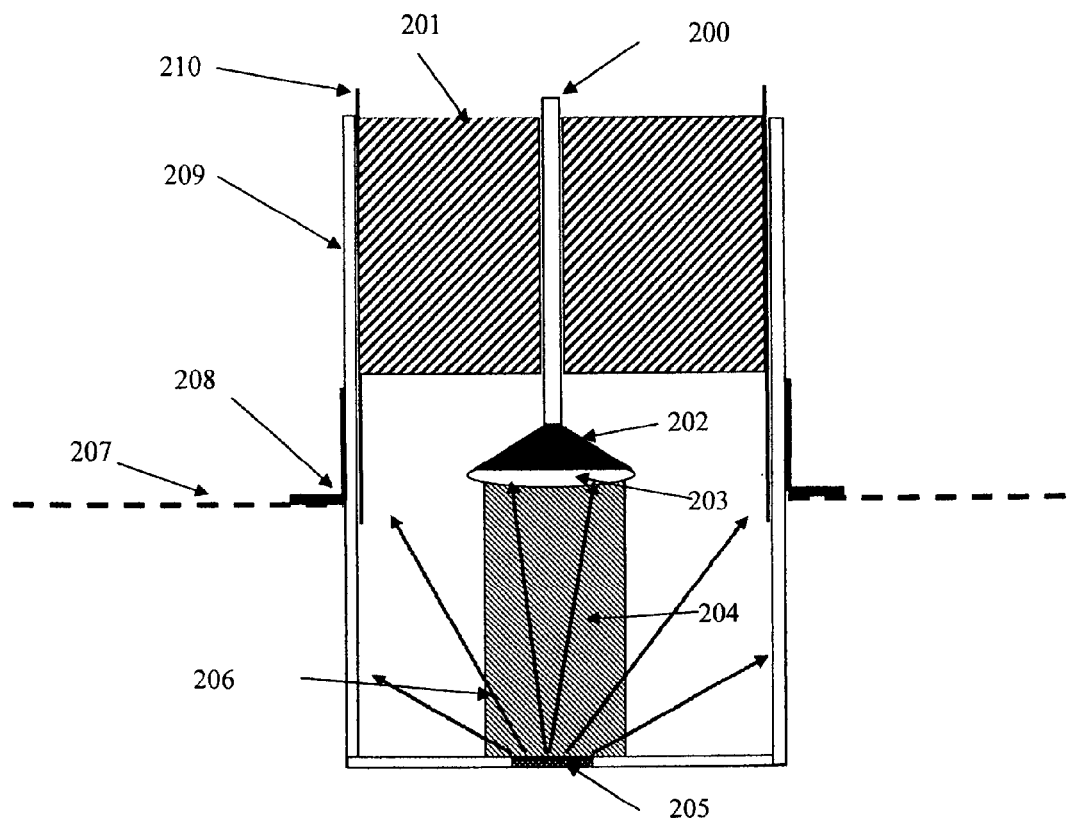

It is also possible to use a combination of a fiber-based system and the type of interface described in FIG. 9. In FIG. 9, a method for using a fiber or fiber bundle 200 is shown. The fiber system can be anchored into the disposable shell 209 through a ferrule 201 or other suitable retention system, or the shell can be detachable from the metal housing of the reader 210. The decision on how much is disposable is dictated by the trade-offs between cost and ease of design. The diverging light 202 from the fiber or fiber bundle will preferably, but not necessarily be collimated using a lens or lens system 203. If such a lens system is used, the collimated light 204 will be precisely incident on the fluorescent dye spot 205. If the excitation is not collimated, it will continue to impinge on the fluorescent dye spot but will be a general illumination of the area rather than a focused beam incident upon the fluorescent dye spot. The fluorophore absorbs the excitation light and then emits fluorescent light 206. This fluorescent signal then impinges upon the fiber or fiber bundle 200 and returns to the transmitter. The fluorescent dye spot and fiber in FIG. 9 are also mounted in a disposable shell 209 comprised of a preferably USP and FDA regulation compliant material, that is optically transparent and moldable or machinable. This disposable shell can also be inserted into a port 208 that is affixed to the disposable bioreactor's lining 207.

Figure 10:
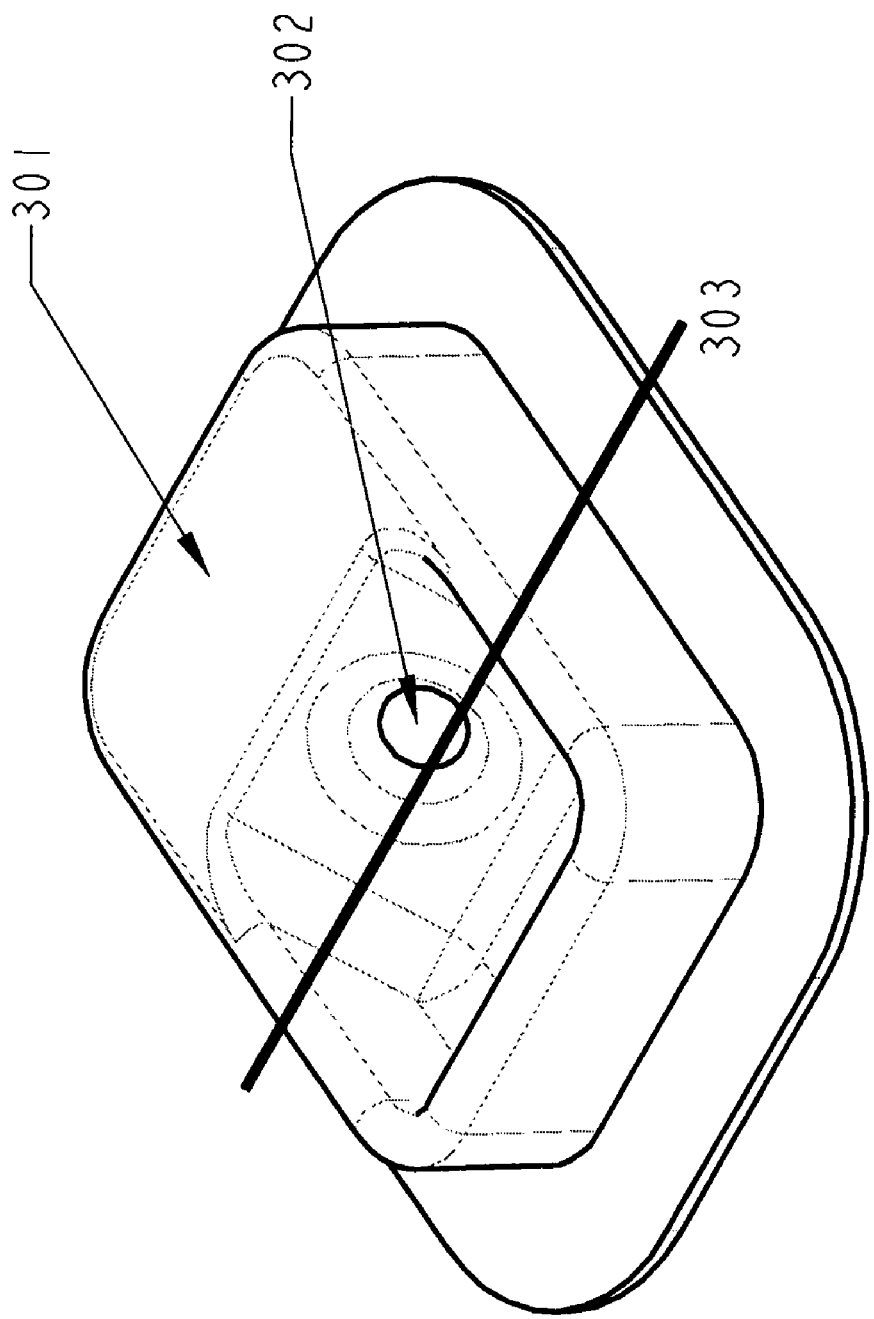
FIG. 10 shows a specific type of port used on a pillow bag type of disposable bioreactor. This port has a trough that also allows the sensors to always be immersed in the bioreactor's fluid during a rocking period.

FIG. 10 shows another style of port design that is affixed to the inside of a Wave Biotech type pillow bag. The port 301 is affixed to the inside of the bag, and by its design the window to the optical system 302 is always submerged in liquid when the bag is rocked (rotated) around axis 303.

Figure 11:
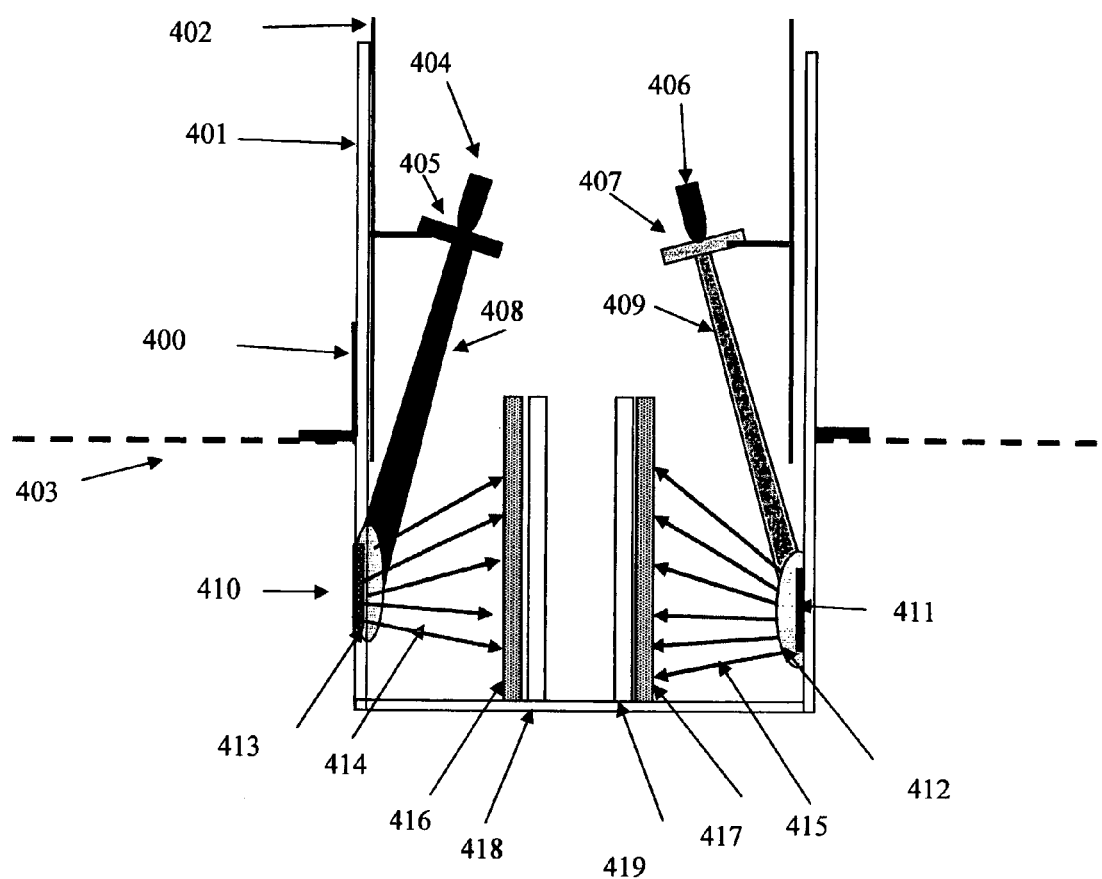
FIG. 11 shows a disposable optical sensor that uses two physically distinct fluorophores to detect to analytes. The analytes can be the same or different.

FIG. 11 shows a port and disposable sensor assembly similar to that shown in FIG. 8 except that it utilizes two distinct fluorophores located at different positions on disposable sheath 401. This assembly can also be used with an optical fiber based system like the one shown in FIG. 9, and/or can also utilize a multitude of fluorophores which can target different analytes of interest, or can target one analyte multiple times to give a redundant system. In FIG. 11, 400 is the hollow port member which is affixed to the disposable bioreactor liner 403. The entire reader 402 which houses the permanent optics and electronics (not shown) is inserted into a disposable sheath 401 which is made using a biocompatible material meeting all the aforementioned standards and requirements. In the reader, 404 is a LED or suitable light source which is optically filtered by 405. The filter 405 passes the excitation light 408 matching the first fluorophore 410. The emitted fluorescent signal 414 is collected by a lens 413 or other suitable optical train. The signal passes through optical filter 416 which substantially blocks all but the wavelengths emitted by the fluorophore. The signal light is converted to an electrical signal by the PIN photodiode or other suitable photodetector 418. Similarly, another LED or suitable light source 406 is optically filtered by 407. The filter 407 passes the excitation light 409 matching the second fluorophore 411. The emitted fluorescent signal 415 is collected by a lens 412 or other suitable optical train. The signal passes through optical filter 417 which substantially blocks all but the wavelengths emitted by the fluorophore. The signal light is converted to an electrical signal by the PIN photodiode or suitable photodetector 419.

Figure 12:
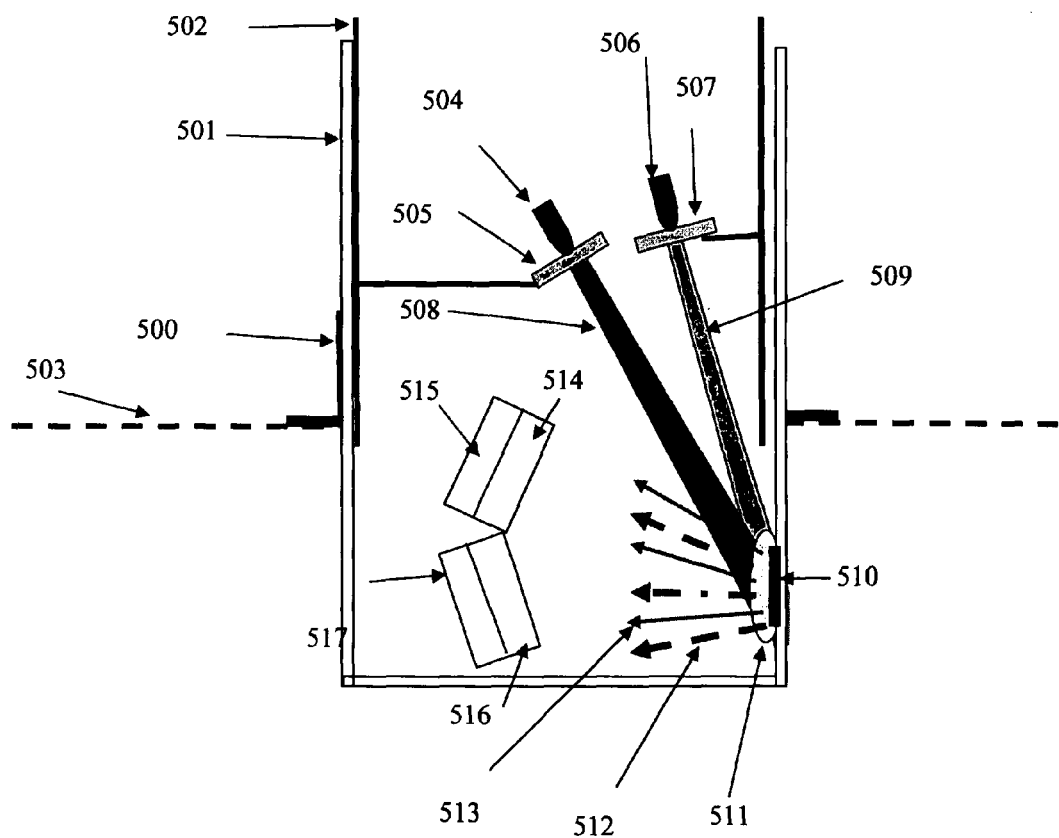
FIG. 12 shows a disposable optical sensor that uses a single spot that contains multiple fluorophores. The excitation source can be a multiple wavelength source as shown, or can be a single source.

FIG. 12 shows a system where the fluorophores do not have to be physically separated from each other. The spot can be made up of several regions containing different fluorophores, or all of the fluorophores can be distributed uniformly over the area of the spot. In FIG. 12, 500 is a port which is affixed to the disposable bioreactor or lining 503. The reader 502 which houses the permanent optics and electronics (not shown) is inserted into a disposable sheath 501 which is preferably fabricated from a biocompatible material meeting the aforementioned standards and requirements. The spot 510 which can contain multiple fluorophores uses a lens or other suitable optical system 511 to direct the multiple fluorescent signals 512 and 513 to multiple optical filters 514 and 516. These optical filters will typically allow only one of the emitted signals to pass through and block the other. The signals fluorescent signals 512 and 513 will be detected using PIN photodiodes or other suitable photo-detectors 515 and 517. This design or reader is suitably referred to as a multi-faceted reader. The fluorophore 510 can be illuminated by one or two appropriate light sources depending on the specific fluorophore or combination of fluorophores being utilized. It is possible that multiple fluorophores embedded in a single matrix will have an absorption feature broad enough that only one source will be required. FIG. 12 allows for the possibility of multiple sources (e.g.: appropriate LEDs) 504 and 506 supplying excitation light which is passed through optical filters 505 and 507 respectively. Although only two fluorophores are shown, this system can easily be generalized to detect N target analytes using additional fluorophores where N>2.

It should be noted that with any of the embodiments of the present invention, the entire bioreactor and sensor unit can be assembled and gamma radiated prior to shipment. The system is typically irradiated with between 25 kGray and 50 kGray in order to ensure that the system is bio-inactive. The result of this is that the end user receives a sterile disposable bioreactor with sensors in place and ready to use. In some cases, the sterilized system is also pre-filled with media. Likewise, the port assembly of the present invention can be readily configured to receive additional analytical probe components which measure temperature, pressure and/or conductivity.

The invention claimed is:

1. A port assembly for use with a polymeric bioreactor bag said assembly comprising:
   i) a hollow port member comprised at least in part of a material suitable to be fusibly affixed to the wall surface of said bioreactor bag;
   ii) at least one fluorophore spot positioned on said port member;
   iii) conduit means for conveying excitation light from an optical source to said fluorophore, said conduit means being an assembly comprising at least one of a lens, a curved parabolic collimator, a shaped reflector or a wave guide;
   iv) conduit means for conveying fluorescent emission light from said fluorophore to a photo-detector, said conduit means being an assembly comprising at least one of a lens, a curved parabolic collimator, a shaped reflector or a wave guide;
   wherein said excitation light conduit means and said emission light conduit means are different.

2. The port assembly of claim 1 further comprising a foraminous shield fitted to said port member and positioned to shield said fluorophore spot from ambient light, said shield having orifices which permit fluid contained within said bioreactor bag to contact said fluorophore.

3. The port assembly of claim 1 wherein each of said excitation light conduit means is a curved parabolic collimator.

4. The port assembly of claim 1 wherein said excitation light conduit means is a slab waveguide.

5. The port assembly of claim 1 wherein components ii) through iv) are initially separate from component i) and are installed in the hollow port member subsequent to the port member being affixed to the bioreactor bag.

6. The port assembly of claim 1 wherein said fluorophore is sensitive to at least one of oxygen, pH, $CO_2$, glucose, or lactate.

7. The port assembly of claim 6 wherein said fluorophore is sensitive to oxygen or pH.

8. The port assembly of claim 1 wherein said optical source is a light emitting diode.

9. The port assembly of claim 1 wherein said port member is fabricated from a biocompatible, FDA and USP regulation compliant, animal component derived free material.

10. The port assembly of claim 1 wherein plural fluorophore spots sensitive to different analytes are separately positioned on said port member.

11. The port assembly of claim 10 wherein said photodetector comprises a multi-faceted reader.

12. The port assembly of claim 1 wherein a single spot contains a plurality of fluorophores sensitive to different analytes.

13. The port assembly of claim 1 wherein said fluorophore is a naturally occurring auto-fluorescing material.

14. The port assembly of claim 1 wherein said hollow port member is configured to receive additional analytical probe components.

15. The port assembly of claim 12 wherein said additional analytical probe components measure temperature, pressure and/or conductivity.

* * * * *